(12) United States Patent
Dobrawa et al.

(10) Patent No.: US 8,754,027 B2
(45) Date of Patent: Jun. 17, 2014

(54) QUATERNIZED POLYETHULENIMINES WITH A HIGH ETHOXYLATION DEGREE

(71) Applicant: BASF SE, Ludwigshafen (DE)

(72) Inventors: Rainer Dobrawa, Ludwigshafen (DE); Sophia Ebert, Mannheim (DE); Stefano Scialla, Rome (IT); Frank Hulskotter, Bad Dürkheim (DE); Gloria Di Capua, Ardea (IT); Patrick Delplancke, Strombeek-Bever (BE); Marc Evers, Strombeek-Bever (BE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/890,391

(22) Filed: May 9, 2013

(65) Prior Publication Data

US 2013/0324451 A1    Dec. 5, 2013

Related U.S. Application Data

(60) Provisional application No. 61/645,648, filed on May 11, 2012.

(51) Int. Cl.
C11D 7/22 (2006.01)
C11D 7/26 (2006.01)
C11D 7/32 (2006.01)

(52) U.S. Cl.
USPC ............ 510/504; 510/499; 510/505; 510/506

(58) Field of Classification Search
USPC .................................. 510/499, 504, 505, 506
See application file for complete search history.

(56) References Cited

U.S. PATENT DOCUMENTS

| | | |
|---|---|---|
| 3,812,044 A | 5/1974 | Connor et al. |
| 3,915,903 A | 10/1975 | Wise |
| 4,246,612 A | 1/1981 | Berry et al. |
| 4,663,071 A | 5/1987 | Bush et al. |
| 4,810,410 A | 3/1989 | Diakun et al. |
| 5,114,611 A | 5/1992 | Van Kralingen et al. |
| 5,227,084 A | 7/1993 | Martens et al. |
| 6,008,181 A | 12/1999 | Cripe et al. |
| 6,020,303 A | 2/2000 | Cripe et al. |
| 6,060,443 A | 5/2000 | Cripe et al. |
| 2007/0275868 A1 | 11/2007 | Cooremans et al. |
| 2009/0215662 A1 | 8/2009 | Boeckh et al. |
| 2011/0103998 A1 | 5/2011 | Ratchev et al. |

FOREIGN PATENT DOCUMENTS

| | | |
|---|---|---|
| EP | 111965 A2 | 6/1984 |
| EP | 0458397 A2 | 11/1991 |
| EP | 0458398 A2 | 11/1991 |
| EP | 0957156 A1 | 11/1999 |
| WO | WO-99/05082 A1 | 2/1999 |
| WO | WO-99/05084 A1 | 2/1999 |
| WO | WO-99/05241 A1 | 2/1999 |
| WO | WO-99/05242 A1 | 2/1999 |
| WO | WO-99/05243 A1 | 2/1999 |
| WO | WO-99/05244 A1 | 2/1999 |
| WO | WO-99/06521 A1 | 2/1999 |
| WO | WO-99/07656 A2 | 2/1999 |
| WO | WO-00/23548 A1 | 4/2000 |
| WO | WO-00/23549 A1 | 4/2000 |
| WO | WO-2005063850 A1 | 7/2005 |
| WO | WO2006/113315 | * 10/2006 |
| WO | WO-2006108856 A2 | 10/2006 |
| WO | WO-2006113314 A1 | 10/2006 |
| WO | WO-2008146194 A1 | 12/2008 |
| WO | WO-2009/060059 A2 | 5/2009 |
| WO | WO-2010020765 A1 | 2/2010 |
| WO | WO-2011051646 A1 | 5/2011 |

OTHER PUBLICATIONS

European Search Report for EP 12167671, dated Aug. 28, 2012.
Scherr, G., et al., "Imines, cyclic", Kirk-Othmer Encyclopedia of Chemical Technology, John Wiley & Sons, Inc., (2000), pp. 1-34.
Steuerle, U., et al., "Aziridines", Ullmann's Encyclopedia of Industrial Chemistry, Wiley-VCH Verlag GmbH, (2012), pp. 515-522.

* cited by examiner

Primary Examiner — Gregory R Delcotto
(74) Attorney, Agent, or Firm — Drinker Biddle & Reath LLP

(57) ABSTRACT

The present invention relates to an ethoxylated polyethylenimine polymer comprising (1) a polyethyleneimine backbone, (2) a polyoxyethylene chain wherein the polyoxyethylene chain has an average of 40 to 90 ethyleneoxide units per unit of NH in the polyethyleneimine backbone, (3) a quaternization degree of from 1% to less than 50%.

3 Claims, No Drawings

QUATERNIZED POLYETHULENIMINES WITH A HIGH ETHOXYLATION DEGREE

CROSS-REFERENCE TO RELATED APPLICATIONS

This application claims benefit (under 35 U.S.C. §119(e)) of U.S. Provisional Application No. 61/645,648, filed May 11, 2012, which is incorporated by reference herein in its entirety.

BRIEF SUMMARY OF THE INVENTION

The present invention relates to an ethoxylated polyethylenimine polymer comprising (1) a polyethyleneimine backbone, (2) an ethoxylation modification consisting of the replacement of a hydrogen atom by a polyoxyethylene chain having an average of 40 to 90 ethoxy units per unit of NH in the polyethyleneimine backbone, (3) a quaternization degree of the nitrogen atoms present in the polyethyleneimine backbone which lies in the range of from 1% to less than 50%.

BACKGROUND OF THE INVENTION

Surface cleaning with liquid detergents poses an ongoing problem for consumers. Consumers utilizing liquid detergents as a light-duty liquid dishwashing detergent composition or as a hard surface cleaning composition frequently find surface imperfections such as soil residues, streaks, film and/or spots after washing. Besides, consumers prefer cleaning compositions to be dried faster after the cleaning process. Hence, there remains a need for liquid cleaning compositions which not only clean hard surfaces, but also deliver improved shine and fast-drying.

It is an object of the present invention to provide polymers which are suitable as an additive to cleaning compositions for hard surfaces and which deliver improved shine and fast-drying benefit when used for light-duty dishwashing or for hard surface cleaning.

The use of polyalkyleneimines in cleaning compositions is known. Traditionally, polyalkyleneimines have been used in laundry detergents to provide soil suspension benefits. Polyethyleneimines have also been used in hard surface cleaning compositions to provide different benefits. WO2011/051646 discloses a method of treating hard surfaces to improve soil resistance, particularly resistance to oily soils, which comprises applying to the surface a composition comprising a quaternised polyamine which has been block propoxylated and then block ethoxylated. WO2010/020765 discloses the use of a composition comprising a polyalkyleneimine and/or a salt or derivative thereof for the prevention of corrosion of non-metallic inorganic items during a washing or rinsing process.

US2007/0275868A1 reads on a liquid detergent composition comprising an alkoxylated polyethylenimine with one or two alkoxylation modification per nitrogen atom. The degree of permanent quaternization may be from 0% to 30% of the polyethyleneimine backbone nitrogen atoms. WO2006/108856 reads on an amphiphilic water-soluble alkoxylated polyalkyleneimines comprising ethylenoxy and propylenoxy units and having a degree of quaternization of up to 50% for use as additives for laundry detergents and cleaning compositions.

WO2009/060059 describes amphiphilic water-soluble alkoxylated polyalkyleneimines comprising ethylenoxy and propylenoxy units for use as additives for laundry detergents.

A DETAILED DESCRIPTION OF THE INVENTION

It has surprisingly been found that the polymers of the present invention are not only effective in cleaning surfaces, but also provide an improved shine benefit when used for light-duty dishwashing or for hard surface cleaning.

Ethoxylated Polyethyleneimine Polymer

The ethoxylated polyethyleneimine of the present invention has the general structure of formula (I):

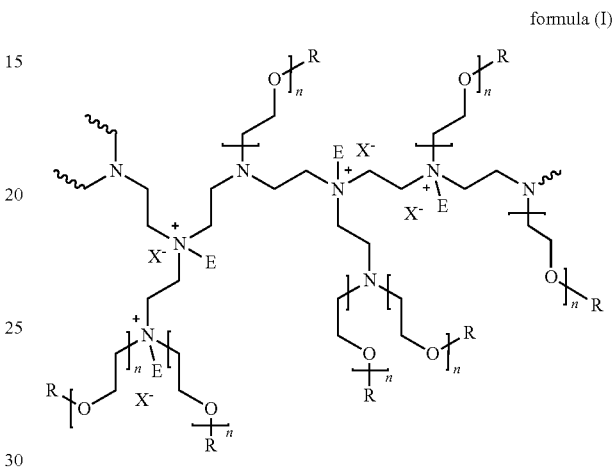

formula (I)

wherein n has a value which lies in the range of from 40 to 90, R of formula (I) is selected from hydrogen, a $C_1$-$C_4$ alkyl and mixtures thereof, E represents a $C_1$-$C_{12}$ alkyl moiety, $X^-$ represents a suitable water soluble counterion and the degree of quaternization of the nitrogen atoms present in the polyethyleneimine backbone lies in the range of from 1% to 50%, more preferably from 5% to 40% and especially from 15% to 30%. Preferably the R is a hydrogen atom. Quaternization is preferably achieved by reaction with dimethyl sulfate.

In a preferred embodiment n has a value which lies in the range of from 45 to 80, even more preferably in the range of from 50 to 80.

In another preferred embodiment the polyethyleneimine backbone has a weight average molecular weight of from 400 to 10000 g/mol, more preferably of from 400 to 6000 g/mol, even more preferably of from 400 to 1800 g/mol.

The substitution of the polyethyleneimine backbone includes: (1) one or two ethoxylation modifications per nitrogen atom, dependent on whether the modification occurs at an internal nitrogen atom or at a terminal nitrogen atom in the polyethyleneimine backbone. The ethoxylation modification consists of the replacement of a hydrogen atom by a polyoxyethylene chain having an average of about 40 to about 90 ethoxy units per modification, preferably about 45 to about 80 ethoxy units, and more preferably about 50 to about 80 ethoxy units. The terminal ethoxy unit of the ethoxylation modification is capped with hydrogen, a $C_1$-$C_4$ alkyl or mixtures thereof. (2) quaternization of a tertiary nitrogen atom, bearing 0, 1, or 2 polyoxyethylene chains. The quaternization is achieved preferably by introducing $C_1$-$C_{12}$ alkyl, aryl or alkylaryl groups and may be undertaken in a customary manner by reaction with corresponding alkyl-, alkylaryl-, halides and dialkylsulfates.

The degree of quaternization of the nitrogen atoms present in the polyethyleneimine backbone lies in the range of from 1% to 50%, preferably from 5% to 40%, most preferably from 15% to 30% of the polyethyleneimine backbone nitrogen atoms.

For example, but not limited to, below is shown possible modifications to terminal nitrogen atoms in the polyethyleneimine backbone where R represents an ethylene spacer and E represents a $C_1$-$C_{12}$ alkyl unit and $X^-$ represents a suitable water soluble counterion, such as chlorine, bromine or iodine, sulphate (i.e. —O—SO3H or —O—SO3-), alkylsulfonate such as methylsulfonate, arylsulfonate such as tolylsulfonate, and alkyl sulphate, such as methosulphate (i.e. —O—SO2-OMe).

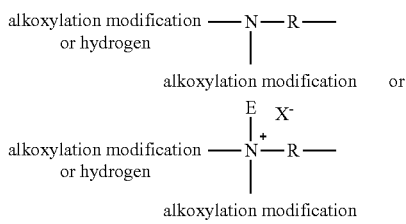

Also, for example, but not limited to, below is shown possible modifications to internal nitrogen atoms in the polyethyleneimine backbone where R represents an ethylene spacer, E represents a $C_1$-$C_{12}$ alkyl unit and $X^-$ represents a suitable water soluble counterion.

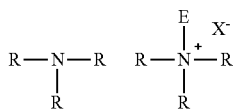

These polyethyleneimines can be prepared, for example, by polymerizing ethyleneimine in the presence of a catalyst such as carbon dioxide, sodium bisulfite, sulfuric acid, hydrogen peroxide, hydrochloric acid, acetic acid, as described in G. Scherr, U. Steuerle and R. Fikentscher: "Imines, Cyclic" in Kirk-Othmer Encyclopedia of Chemical Technology and U. Steuerle, R. Feuerhake: "Aziridines" in Ullmann's Encyclopedia of Industrial Chemistry.

The inventive alkoxylated polyalkyleneimines may be prepared in a known manner by reaction of polyalkylene imines with alkylene oxides. Suitable alkylene oxides are $C_2$-$C_{20}$ alkylene oxides like ethylene oxide, propylene oxide, butylene oxide, pentene oxide, hexene oxide, decene oxide, dodecene oxide etc. Polyalkylene imines are reacted with one single alkylene oxide or combinations of two or more different alkylene oxides. Using two or more different alkylene oxides, the resulting polymer can be obtained as a block-wise structure or a random structure. One preferred procedure consists in initially undertaking only an incipient alkoxylation of the polyalkylene imine in a first step. In this step, the polyalkylene imine is reacted only with a portion of the total amount of alkylene oxide used, which corresponds to about 1 mol of alkylene oxide per mole of NH moiety. This reaction is undertaken generally in the absence of a catalyst in an aqueous solution at a reaction temperature from about 70 to about 200° C. and preferably from about 80 to about 160° C. This reaction may be affected at a pressure of up to about 10 bar, and in particular up to about 8 bar.

In a second step, the further ethoxylation is then effected by subsequent reaction with the remaining amount of ethylene oxide. The further ethoxylation is undertaken typically in the presence of a basic catalyst. Examples of suitable catalysts are alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. Preference is given to the alkali metal hydroxides and the alkali metal alkoxides, particular preference being given to potassium hydroxide and sodium hydroxide. Typical use amounts for the base are from 0.05 to 10% by weight, in particular from 0.5 to 2% by weight, based on the total amount of polyalkyleneimine and alkylene oxide.

The further ethoxylation may be undertaken in substance (variant a)) or in an organic solvent (variant b)). In variant a), the aqueous solution of the incipiently alkoxylated polyalkylenimine obtained in the first step, after addition of the catalyst, is initially dewatered. This can be done in a simple manner by heating to from about 80 to about 150° C. and distilling off the water under a reduced pressure of from about 0.01 to about 0.5 bar. The subsequent reaction with the ethylene oxide is effected typically at a reaction temperature from about 70 to about 200° C. and preferably from about 100 to about 180° C. The subsequent reaction with the alkylene oxide is effected typically at a pressure of up to about 10 bar and in particular up to 8 bar. The reaction time of the subsequent reaction with the alkylene oxide is generally about 0.5 to about 4 hours. Suitable organic solvents for variant b) are in particular nonpolar and polar aprotic organic solvents. Examples of particularly suitable nonpolar aprotic solvents include aliphatic and aromatic hydrocarbons such as hexane, cyclohexane, toluene and xylene. Examples of particularly suitable polar aprotic solvents are ethers, in particular cyclic ethers such as tetrahydrofuran and dioxane, N,N-dialkylamides such as dimethylformamide and dimethylacetamide, and N-alkyllactams such as N-methylpyrrolidone. It is of course also possible to use mixtures of these organic solvents. Preferred organic solvents are xylene and toluene.

In variant b), the solution obtained in the first step, after addition of catalyst and solvent, is initially dewatered, which is advantageously done by separating out the water at a temperature of from about 120 to about 180° C., preferably supported by a gentle nitrogen stream. The subsequent reaction with the alkylene oxide may be effected as in variant a). In variant a), the alkoxylated polyalkylenimine is obtained directly in substance and may be converted if desired to an aqueous solution. In variant b), the organic solvent is typically removed and replaced by water. The products may, of course, also be isolated in substance.

The quaternization of alkoxylated polyethyleneimines is achieved preferably by introducing C1-C12 alkyl, aryl or alkylaryl groups and may be undertaken in a customary manner by reaction with corresponding alkyl-, alkylaryl-, halides and dialkylsulfates, as described for example in WO2009060059.

The quaternization of ethoxylated polyethyleneimines is achieved preferably by reacting the amines with at least one alkylating compound, which is selected from the compounds of the formula EX, wherein E is C1-C12 alkyl, aryl or alkyl and X is a leaving group, which is capable of being replaced by nitrogen (and C2-C6 alkylene oxide, especially ethylene oxide or propylene oxide).

Suitable leaving groups X are halogen, especially chlorine, bromine or iodine, sulphate (i.e. —OSO3H or —OSO3-), alkylsulfonate such as methylsulfonate, arylsulfonate such as tolylsulfonate, and alkyl sulphate, such as methosulphate (i.e. —OSO2OMe). Preferred alkylating agents EX are C1-C12 alkyl halides, bis(C1-C12-alkyl)sulfates, and benzyl halides. Examples of such alkylating agents are ethyl chloride, ethyl bromide, methyl chloride, methyl bromide, benzyl chloride, dimethyl sulphate, diethyl sulphate.

The amount of alkylating agent determines the amount of quaternization of the amino groups in the polymer, i.e. the amount of quaternized moieties.

The amount of the quaternized moieties can be calculated from the difference of the amine number in the non-quaternized amine and the quaternized amine.

The amine number can be determined according to the method described in DIN 16945.

The reaction can be carried out without any solvent, However, a solvent or diluent like water, acetonitrile, dimethylsulfoxide, N-Methylpyrrolidone, etc. may be used. The reaction temperature is usually in the range from 10° C. to 150° C. and is preferably from 50° C. to 110° C.

For the purpose of the present invention, "consisting essentially of" is to be understood in the sense that the copolymer according to the invention might contain a certain amount of impurities or other alkyleneoxide groups other than ethylene oxide. Thus the inventive polymer might contain up to 5 alkylenoxide groups other than ethylene oxide per mol of NH in the polyethyleneimine backbone, such as propylene oxide or butylene oxide.

Compositions Comprising the Ethoxylated Polyethyleneimine Polymer According to the Invention.

The ethoxylated polyethyleneimine polymer according to the invention may be comprised in an amount of from 0.001 to 10% by weight, more preferably from 0.01 wt % to 1.5 wt % and most preferably from 0.05% to 1.0% by weight in a hard surface cleaning detergent composition, a hand dishwashing detergent composition or an automatic dishwashing detergent composition. The composition comprising the ethoxylated polyethyleneimine polymer according to the invention may be in a form selected from the group consisting of a liquid, a gel, and a solid. Preferably, the composition comprising the polymer according to the present invention is a liquid cleaning composition or a gel cleaning composition.

The ethoxylated polyethyleneimine polymer according to the invention may also be comprised in chemical technical applications, car wash, cosmetics, paper and cardboard manufacturing, leather and textile industry.

In a preferred embodiment, the hard surface cleaning composition comprising the ethoxylated polyalkylenimine polymer according to the invention is used to provide fast drying and/or to deliver shine on household hard surfaces. In an alternatively preferred embodiment, the hand dishwashing detergent composition comprising the polymer according to the invention is used to provide fast drying and/or to deliver shine on dishes, flatware, glassware, cutlery, etc. in a hand dishwashing cleaning operation. In another preferred embodiment, the automatic dishwashing composition comprising the polymer according to the invention is used to provide fast drying and/or to deliver shine on dishes, flatware, glassware, cutlery, etc. in an automatic dishwashing operation.

In one preferred embodiment, the composition is a hard surface cleaning composition, the composition comprises from about 70% to about 99%, preferably from about 75% to about 95%, and more preferably from about 80% to about 95% by weight of the total composition, of water. Alternatively, in another preferred embodiment, the composition is a hand dishwashing detergent composition, the composition comprises from about 30% to about 95%, preferably from about 40% to about 80%, and more preferably from about 50% to about 75% by weight of the total composition, of water.

In the preferred embodiment wherein the composition is a hard surface cleaning composition, the composition has a pH from about 2 to about 14, preferably from about 2 to about 10, more preferably from about 2 to about 9.5, and even more preferably from about 2.1 to about 8, as is measured at 25° C. In the preferred embodiment wherein the composition is a hand dishwashing detergent composition, the composition has a pH from about 3 to about 14, preferably from about 6 to about 13, most preferably from about 8 to about 11.

The hard surface cleaning composition, the hand dishwashing detergent composition and the automatic dishwashing composition, all comprising the ethoxylated polyalkylenimine polymer according to the invention, and used to provide fast drying and/or to deliver shine on household hard surfaces may contain the following further ingredients:

Surfactant

Surfactants may be present in amounts from 0 to 15% by weight, preferably from 0.1% to 10%, and most preferably from 0.25% to 8% by weight of the total composition.

Surfactants may be desired herein as they contribute to the cleaning performance of the liquid cleaning compositions of the present invention. Suitable surfactants are selected from the group consisting of a nonionic surfactant or a mixture thereof; an anionic surfactant or a mixture thereof; an amphoteric surfactant or a mixture thereof; a zwitterionic surfactant or a mixture thereof; a cationic surfactant or a mixture thereof; and mixtures thereof.

In the preferred embodiment wherein the composition is a hard surface cleaning composition, the composition comprises from about 1% to about 60%, preferably from about 5% to about 30%, and more preferably from about 10% to about 25% by weight of the total composition of a surfactant.

In the preferred embodiment wherein the composition is a hand dishwashing detergent composition, the composition may comprise from about 5% to about 80%, preferably from about 10% to about 60%, more preferably from about 12% to about 45% by weight of the total composition of a surfactant. In preferred embodiments, the surfactant herein has an average branching of the alkyl chain(s) of more than about 10%, preferably more than about 20%, more preferably more than about 30%, and even more preferably more than about 40% by weight of the total surfactant.

Nonionic Surfactant

In one preferred embodiment, the liquid cleaning composition comprises a nonionic surfactant. Suitable nonionic surfactants may be alkoxylated alcohol nonionic surfactants, which can be readily made by condensation processes which are well-known in the art.

Accordingly, preferred alkoxylated alcohols for use herein are nonionic surfactants according to the formula $R^1O(E)_e(P)_pH$ where $R^1$ is a hydrocarbon chain of from about 2 to about 24 carbon atoms, E is ethylene oxide, P is propylene oxide, and e and p which represent the average degree of, respectively ethoxylation and propoxylation, are of from about 0 to about 24 (with the sum of e+p being at least 1). Preferably, the hydrophobic moiety of the nonionic compound can be a primary or secondary, straight or branched alcohol having from about 8 to about 24 carbon atoms.

Preferably, the nonionic surfactant is comprised in a typical amount of from about 2% to about 40%, preferably from about 3% to about 30% by weight of the liquid cleaning composition, and preferably from about 3 to about 20% by weight of the total composition.

Also suitable are alkylpolyglycosides having the formula $R^3O(C_nH_{2n}O)_t(glycosyl)_z$ (formula (III)), wherein $R^3$ of formula (III) is selected from the group consisting of an alkyl or a mixture thereof; an alkyl-phenyl or a mixture thereof; a hydroxyalkyl or a mixture thereof; a hydroxyalkylphenyl or a mixture thereof; and mixtures thereof, in which the alkyl group contains from about 10 to about 18, preferably from about 12 to about 14 carbon atoms; n of formula (III) is about 2 or about 3, preferably about 2; t of formula (III) is from about 0 to about 10, preferably about 0; and z of formula (III) is from about 1.3 to about 10, preferably from about 1.3 to about 3, most preferably from about 1.3 to about 2.7. The glycosyl is preferably derived from glucose. Also suitable are alkyl glycerol ether and sorbitan ester.

Also suitable is fatty acid amide surfactant having the formula (IV):

(IV)

wherein $R^6$ of formula (IV) is an alkyl group containing from about 7 to about 21, preferably from about 9 to about 17, carbon atoms, and each $R^7$ of formula (IV) is selected from the group consisting of hydrogen; a $C_1$-$C_4$ alkyl or a mixture thereof; a $C_1$-$C_4$ hydroxyalkyl or a mixture thereof; and a —$(C_2H_4O)_yH$ or a mixture thereof, where y of formula (IV) varies from about 1 to about 3. Preferred amide can be a $C_8$-$C_{20}$ ammonia amide, a monoethanolamide, a diethanolamide, and an isopropanolamide.

In one preferred embodiment, the weight ratio of total surfactant to nonionic surfactant is from about 2 to about 10, preferably from about 2 to about 7.5, more preferably from about 2 to about 6.

Anionic Surfactant

Suitable anionic surfactants for use in the liquid cleaning composition can be a sulfate, a sulfosuccinate, a sulfoacetate, and/or a sulphonate; preferably an alkyl sulfate and/or an alkyl ethoxy sulfate; more preferably a combination of an alkyl sulfate and/or an alkyl ethoxy sulfate with a combined ethoxylation degree less than about 5, preferably less than about 3, more preferably less than about 2.

Sulphate or sulphonate surfactant is typically present at a level of at least about 5%, preferably from about 5% to about 40%, and more preferably from about 15% to about 30%, and even more preferably at about 15% to about 25% by weight of the liquid cleaning composition.

Suitable sulphate or sulphonate surfactants for use in the liquid cleaning composition include water-soluble salts or acids of $C_8$-$C_{14}$ alkyl or hydroxyalkyl, sulphate or sulphonates. Suitable counterions include hydrogen, alkali metal cation or ammonium or substituted ammonium, but preferably sodium. Where the hydrocarbyl chain is branched, it preferably comprises a $C_{1-4}$ alkyl branching unit. The average percentage branching of the sulphate or sulphonate surfactant is preferably greater than about 30%, more preferably from about 35% to about 80%, and most preferably from about 40% to about 60% of the total hydrocarbyl chain.

The sulphate or sulphonate surfactants may be selected from a $C_{11}$-$C_{18}$ alkyl benzene sulphonate (LAS), a $C_8$-$C_{20}$ primary, a branched-chain and random alkyl sulphate (AS); a $C_{10}$-$C_{18}$ secondary (2,3) alkyl sulphate; a $C_{10}$-$C_{18}$ alkyl alkoxy sulphate (AE$_x$S) wherein preferably x is from 1-30; a $C_{10}$-$C_{18}$ alkyl alkoxy carboxylate preferably comprising about 1-5 ethoxy units; a mid-chain branched alkyl sulphate as discussed in U.S. Pat. No. 6,020,303 and U.S. Pat. No. 6,060,443; a mid-chain branched alkyl alkoxy sulphate as discussed in U.S. Pat. No. 6,008,181 and U.S. Pat. No. 6,020,303; a modified alkylbenzene sulphonate (MLAS) as discussed in WO 99/05243, WO 99/05242, WO 99/05244, WO 99/05082, WO 99/05084, WO 99/05241, WO 99/07656, WO 00/23549, and WO 00/23548; a methyl ester sulphonate (MES); and an alpha-olefin sulphonate (AOS).

The paraffin sulphonate may be monosulphonate or disulphonate and usually are mixtures thereof, obtained by sulphonating a paraffin of about 10 to about 20 carbon atoms. Preferred sulphonates are those of $C_{12-18}$ carbon atoms chains and more preferably they are $C_{14-17}$ chains.

Also suitable are the alkyl glyceryl sulphonate surfactant and/or alkyl glyceryl sulphate surfactant. A mixture of oligomeric alkyl glyceryl sulphonate and/or sulfate surfactant selected from a dimmer or a mixture thereof; a trimer or a mixture thereof; a tetramer or a mixture thereof; a pentamer or a mixture thereof; a hexamer or a mixture thereof; a heptamer or a mixture thereof; and mixtures thereof; wherein the alkyl glyceryl sulphonate and/or sulfate surfactant mixture comprises from about 0% to about 60% by weight of the monomers.

Other suitable anionic surfactants are alkyl, preferably dialkyl sulfosuccinate and/or sulfoacetate. The dialkyl sulfosuccinate may be a $C_{6-15}$ linear or branched dialkyl sulfosuccinate. The alkyl moiety may be symmetrical (i.e., the same alkyl moieties) or asymmetrical (i.e., different alkyl moiety.es). Preferably, the alkyl moiety is symmetrical.

Most common branched anionic alkyl ether sulphates are obtained via sulfation of a mixture of the branched alcohols and the branched alcohol ethoxylates. Also suitable are the sulfated fatty alcohols originating from the Fischer & Tropsh reaction comprising up to about 50% branching (about 40% methyl (mono or bi) about 10% cyclohexyl) such as those produced from the safol alcohols from Sasol; sulfated fatty alcohols originating from the oxo reaction wherein at least about 50% by weight of the alcohol is $C_2$ isomer (methyl to pentyl) such as those produced from the Isalchem® alcohols or Lial® alcohols from Sasol; the sulfated fatty alcohols originating from the modified oxo reaction wherein at least about 15% by weight of the alcohol is $C_2$ isomer (methyl to pentyl) such as those produced from the Neodol® alcohols from Shell.

Zwitterionic Surfactant and Amphoteric Surfactant

The zwitterionic and amphoteric surfactants for use in the liquid cleaning composition can be comprised at a level of from about 0.01% to about 20%, preferably from about 0.2% to about 15%, more preferably from about 0.5% to about 10% by weight of the hand dishwashing detergent composition.

Suitable zwitterionic surfactant in the preferred embodiment wherein contains both basic and acidic groups which form an inner salt giving both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylate and sulphonate, although other groups like sulfate, phosphonate, and the like can be used.

The liquid cleaning compositions may preferably further comprise an amine oxide and/or a betaine. Most preferred amine oxides are coconut dimethyl amine oxide or coconut amido propyl dimethyl amine oxide. Amine oxide may have a linear or mid-branched alkyl moiety. Typical linear amine oxides include water-soluble amine oxide containing one $R^4$ $C_{8-18}$ alkyl moiety and 2 $R^5$ and $R^8$ moieties selected from the group consisting of a $C_{1-3}$ alkyl group and a mixtures thereof; and a $C_{1-3}$ hydroxyalkyl group and a mixture thereof. Preferably amine oxide is characterized by the formula $R^4$—$N(R^5)(R^8)$→O wherein $R^4$ is a $C_{8-18}$ alkyl and $R^5$ and $R^8$ are selected from the group consisting of a methyl; an ethyl; a propyl; an isopropyl; a 2-hydroxethyl; a 2-hydroxypropyl; and a 3-hydroxypropyl. The linear amine oxide surfactant, in particular, may include a linear $C_{10}$-$C_{18}$ alkyl dimethyl amine oxide and a linear $C_8$-$C_{12}$ alkoxy ethyl dihydroxy ethyl amine oxide. Preferred amine oxides include linear $C_{10}$, linear $C_{10}$-$C_{12}$, and linear $C_{12}$-$C_{14}$ alkyl dimethyl amine oxides.

As used herein "mid-branched" means that the amine oxide has one alkyl moiety having $n_1$ carbon atoms with one alkyl branch on the alkyl moiety having $n_2$ carbon atoms. The alkyl branch is located on the α carbon from the nitrogen on the alkyl moiety. This type of branching for the amine oxide is also known in the art as an internal amine oxide. The total sum of n1 and n2 is from about 10 to about 24 carbon atoms, preferably from about 12 to about 20, and more preferably from about 10 to about 16. The number of carbon atoms for the one alkyl moiety ($n_1$) should be approximately the same number of carbon atoms as the one alkyl branch ($n_2$) such that the one alkyl moiety and the one alkyl branch are symmetric. As used herein, "symmetric" means that $|n_1-n_2|$ is less than or equal to about 5, preferably about 4, most preferably from about 0 to about 4 carbon atoms in at least about 50 wt %, more preferably at least about 75 wt % to about 100 wt % of the mid-branched amine oxide for use herein.

The amine oxide further comprises two moieties, independently selected from a $C_{1-3}$ alkyl; a $C_{1-3}$ hydroxyalkyl group; or a polyethylene oxide group containing an average of from about 1 to about 3 ethylene oxide groups. Preferably the two moieties are selected from a $C_{1-3}$ alkyl, more preferably both are selected as a $C_1$ alkyl.

Other suitable surfactants include a betaine such an alkyl betaine an alkylamidobetaine, an amidazoliniumbetaine, a sulfobetaine (INCI Sultaines), as well as a phosphobetaine, and preferably meets formula I:

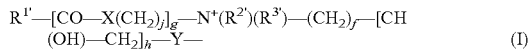
$$R^{1'}\text{—}[CO\text{—}X(CH_2)_j]_g\text{—}N^+(R^{2'})(R^{3'})\text{—}(CH_2)_f\text{—}[CH(OH)\text{—}CH_2]_h\text{—}Y\text{—} \quad (I)$$

wherein
$R^{1'}$ is a saturated or unsaturated $C_{6-22}$ alkyl residue, preferably a $C_{8-18}$ alkyl residue, in particular a saturated $C_{10-16}$ alkyl residue, for example a saturated $C_{12-14}$ alkyl residue;
X is NH, $NR^{4'}$ with $C_{1-4}$ alkyl residue $R^{4'}$, O or S,
j is a number from about 1 to about 10, preferably from about 2 to about 5, in particular about 3,
g is about 0 or about 1, preferably about 1,
$R^{2'}$, $R^{3'}$ are independently a $C_{1-4}$ alkyl residue, potentially hydroxy substituted by such as a hydroxyethyl, preferably by a methyl.
f is a number from about 1 to about 4, in particular about 1, 2 or 3,
h is about 0 or 1, and
Y is selected from COO, $SO_3$, $OPO(OR^{5'})O$ or $P(O)(OR^{5'})O$, whereby $R^{5'}$ is a hydrogen atom H or a $C_{1-4}$ alkyl residue.

Preferred betaines are the alkyl betaine of the formula ($I_a$), the alkyl amido betaine of the formula ($I_b$), the sulfo betaine of the formula ($I_c$), and the Amido sulfobetaine of the formula ($I_d$);

$$R^{1'}\text{—}N^+(CH_3)_2\text{—}CH_2COO^- \quad (I_a)$$

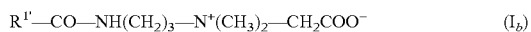
$$R^{1'}\text{—}CO\text{—}NH(CH_2)_3\text{—}N^+(CH_3)_2\text{—}CH_2COO^- \quad (I_b)$$

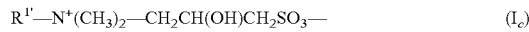
$$R^{1'}\text{—}N^+(CH_3)_2\text{—}CH_2CH(OH)CH_2SO_3\text{—} \quad (I_c)$$

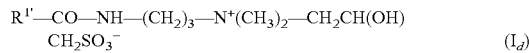
$$R^{1'}\text{—}CO\text{—}NH\text{—}(CH_2)_3\text{—}N^+(CH_3)_2\text{—}CH_2CH(OH)CH_2SO_3^- \quad (I_d)$$

in which $R^{1'}$ has the same meaning as in formula I. Particularly preferred betaines are the carbobetaine, wherein $Y^-$ is [$COO^-$], in particular the carbobetaine of formula ($I_a$) and ($I_b$), more preferred are the alkylamidobetaine of the formula ($I_b$).

Examples of suitable betaines and sulfobetaines are the following (designated in accordance with INCI): almondamidopropyl of betaine, apricotamidopropyl betaine, avocadamidopropyl of betaine, babassuamidopropyl of betaine, behenamidopropyl betaine, behenyl of betaine, betaine, canolamidopropyl betaine, capryl/capramidopropyl betaine, carnitine, cetyl of betaine, co-camidoethyl of betaine, cocamidopropyl betaine, cocamidopropyl hydroxysultaine, coco betaine, coco hydroxysultaine, coco/oleamidopropyl betaine, coco sultaine, decyl of betaine, dihydroxyethyl oleyl glycinate, dihydroxyethyl soy glycinate, dihydroxyethyl stearyl glycinate, dihydroxyethyl tallow glycinate, dimethicone propyl of PG-betaine, drucamidopropyl hydroxysultaine, hydrogenated tallow of betaine, isostearamidopropyl betaine, lauramidopropyl betaine, lauryl of betaine, lauryl hydroxysultaine, lauryl sultaine, milk amidopropyl betaine, milkamidopropyl of betaine, myristamidopropyl betaine, myristyl of betaine, oleamidopropyl betaine, oleamidopropyl hydroxysultaine, oleyl of betaine, olivamidopropyl of betaine, palmamidopropyl betaine, palmitamidopropyl betaine, palmitoyl carnitine, palm kernel amidopropyl betaine, polytetrafluoroethylene acetoxypropyl of betaine, ricinoleamidopropyl betaine, sesamidopropyl betaine, soyamidopropyl betaine, stearamidopropyl betaine, stearyl of betaine, tallowamidopropyl betaine, tallowamidopropyl hydroxysultaine, tallow of betaine, tallow dihydroxyethyl of betaine, undecylenamidopropyl betaine and wheat germ amidopropyl betaine. Preferred betaine is for example cocoamidopropyl betaine.

One particularly preferred zwitterionic surfactants for use in the preferred embodiment wherein the composition is a hard surface cleaning composition is the sulfobetaine surfactant, because it delivers optimum soap scum cleaning benefits.

Examples of particularly suitable sulfobetaine surfactants include tallow bis(hydroxyethyl) sulphobetaine and cocoamido propyl hydroxy sulphobetaine.

Cationic Surfactant

In one preferred embodiment, the liquid cleaning composition can comprise a cationic surfactant present in an effective amount, more preferably from about 0.1% to about 20%, by weight of the liquid cleaning composition. Suitable cationic surfactant is quaternary ammonium surfactant. Suitable quaternary ammonium surfactant is selected from the group consisting of a mono $C_6$-$C_{16}$, preferably a $C_6$-$C_{10}$ N-alkyl or an alkenyl ammonium surfactant or a mixture thereof, wherein the remaining N positions are substituted by a methyl, a hydroxyethyl or a hydroxypropyl group. Another preferred cationic surfactant is a $C_6$-$C_{18}$ alkyl or alkenyl ester of a quaternary ammonium alcohol, such as quaternary chlorine ester. More preferably, the cationic surfactant has formula (V);

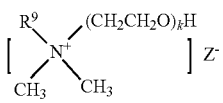 (V)

wherein $R^9$ of formula (V) is a $C_8$-$C_{18}$ hydrocarbyl or a mixture thereof, preferably, a $C_{8-14}$ alkyl, more preferably, a $C_8$, $C_{10}$ or $C_{12}$ alkyl; and Z of formula (V) is an anion, preferably, a chloride or a bromide.

Optional Ingredients

The liquid cleaning composition according to the present invention may comprise a variety of optional ingredients depending on the technical benefit aimed for and the surfaces treated.

Suitable optional ingredients for use herein include an alkaline material or a mixture thereof; an inorganic or organic acid and salt thereof or a mixture thereof; a buffering agent or a mixture thereof; a surface modifying polymer or a mixture thereof; a cleaning polymer or a mixture thereof; a peroxygen bleach or a mixture thereof; a radical scavenger or a mixture thereof; a chelating agent or a mixture thereof; a perfume or a mixture thereof; a dye or a mixture thereof; a hydrotrope or a mixture thereof; a polymeric suds stabilizer or a mixture thereof; a diamine or a mixture thereof; and mixtures thereof.

Solvent

Solvents are generally used to ensure preferred product quality for dissolution, thickness and aesthetics and to ensure better processing. The liquid cleaning composition of the present invention may further comprise a solvent or a mixture thereof, as an optional ingredient. Typically, in the preferred embodiment wherein the composition is a hard surface cleaning composition, the composition may comprise from about 0.1% to about 10%, preferably from about 0.5% to about 5%, and more preferably from about 1% to about 3% by weight of the total composition of a solvent or a mixture thereof. In the preferred embodiment wherein the composition is a hand dishwashing detergent composition, the composition contains from about 0.01% to about 20%, preferably from about 0.5% to about 20%, more preferably from about 1% to about 10% by weight of a solvent.

Suitable solvents herein include $C_1$-$C_6$ alcohols according to the formula $R^{10}$—OH wherein $R^{10}$ is a saturated alkyl group of from about 1 to about 5 carbon atoms, preferably from about 2 to about 4. Suitable alcohols are ethanol, propanol, isopropanol or mixtures thereof. Other suitable alcohols are alkoxylated $C_{1-8}$ alcohols according to the formula $R^{11}$-$(A_q)$-OH wherein $R^{11}$ is a alkyl group of from about 1 to about 8 carbon atoms, preferably from about 3 to about 6, and wherein A is an alkoxy group, preferably propoxy and/or ethoxy, and q is an integer of from 1 to 5, preferably from 1 to 2. Suitable alcohols are butoxy propoxy propanol (n-BPP), butoxy propanal (n-BP), butoxyethanol, or mixtures thereof. Suitable alkoxylated aromatic alcohols to be used herein are those according to the formula $R^{12}$—$(B)_r$—OH wherein $R^{12}$ is an alkyl substituted or non-alkyl substituted aryl group of from about 1 to about 20 carbon atoms, preferably from about 2 to about 15, and more preferably from about 2 to about 10, wherein B is an alkoxy group, preferably a butoxy, propoxy and/or ethoxy, and r is an integer of from 1 to 5, preferably from 1 to 2. A suitable aromatic alcohol to be used herein is benzyl alcohol. Suitable alkoxylated aromatic alcohol is benzylethanol and or benzylpropanol. Other suitable solvent includes butyl diglycolether benzylalcohol, propoxypropoxypropanol (EP 0 859 044) ether and diether, glycol, alkoxylated glycol, $C_6$-$C_{16}$ glycol ether, alkoxylated aromatic alcohol, aromatic alcohol, aliphatic branched alcohol, alkoxylated aliphatic branched alcohol, alkoxylated linear $C_1$-$C_5$ alcohol, linear $C_1$-$C_5$ alcohol, amine, $C_8$-$C_{14}$ alkyl and cycloalkyl hydrocarbon and halohydrocarbon, and mixtures thereof.

Perfume

The liquid cleaning composition of the present invention may comprise a perfume ingredient, or mixtures thereof, in amount up to about 5.0% by weight of the total composition, preferably in amount of about 0.1% to about 1.5%. Suitable perfume compounds and compositions for use herein are for example those described in EP-A-0 957 156 under the paragraph entitled "Perfume", on page 13.

Dye

The liquid cleaning composition according to the present invention may be colored. Accordingly, it may comprise a dye or a mixture thereof. Suitable dyes for use herein are acid-stable dyes. By "acid-stable", it is meant herein a compound which is chemically and physically stable in the acidic environment of the composition herein.

pH Adjustment Agent

Alkaline Material

Preferably, an alkaline material may be present to trim the pH and/or maintain the pH of the composition according to the present invention. The amount of alkaline material is from about 0.001% to about 20%, preferably from about 0.01% to about 10%, and more preferably from about 0.05% to about 3% by weight of the composition.

Examples of the alkaline material are sodium hydroxide, potassium hydroxide and/or lithium hydroxide, and/or the alkali metal oxide, such as sodium and/or potassium oxide, or mixtures thereof. Preferably, the source of alkalinity is sodium hydroxide or potassium hydroxide, preferably sodium hydroxide.

Acid

The liquid cleaning composition of the present invention may comprise an acid. Any acid known to those skilled in the art may be used herein. Typically the composition herein may comprise up to about 20%, preferably from about 0.1% to about 10%, more preferably from about 0.1% to about 5%, even more preferably from about 0.1% to about 3%, by weight of the total composition of an acid.

Suitable acids are selected from the group consisting of a mono- and poly-carboxylic acid or a mixture thereof; a percarboxylic acid or a mixture thereof; a substituted carboxylic acid or a mixture thereof; and mixtures thereof. Carboxylic acids useful herein include $C_{1-6}$ linear or at least about 3 carbon containing cyclic acids. The linear or cyclic carbon-containing chain of the carboxylic acid may be substituted with a substituent group selected from the group consisting of hydroxyl, ester, ether, aliphatic groups having from about 1 to about 6, more preferably from about 1 to about 4 carbon atoms, and mixtures thereof.

Suitable mono- and poly-carboxylic acids are selected from the group consisting of citric acid, lactic acid, ascorbic acid, isoascorbic acid, tartaric acid, formic acid, maleic acid, malic acid, malonic acid, propionic acid, acetic acid, dehydroacetic acid, benzoic acid, hydroxy benzoic acid, and mixtures thereof.

Suitable percarboxylic acids are selected from the group consisting of peracetic acid, percarbonic acid, perboric acid, and mixtures thereof.

Suitable substituted carboxylic acids are selected from the group consisting of an amino acid or a mixture thereof; a halogenated carboxylic acid or a mixture thereof; and mixtures thereof.

Preferred acids for use herein are selected from the group consisting of lactic acid, citric acid, and ascorbic acid and mixtures thereof. More preferred acids for use herein are selected from the group consisting of lactic acid and citric acid and mixtures thereof. An even more preferred acid for use herein is lactic acid.

Salt

In a preferred embodiment, the liquid cleaning composition of the present invention also comprises other salts as the pH buffer. Salts are generally present at an active level of from about 0.01% to about 5%, preferably from about 0.015% to about 3%, more preferably from about 0.025% to about 2.0%, by weight of the composition.

When salts are included, the ions can be selected from magnesium, sodium, potassium, calcium, and/or magnesium, and preferably from sodium and magnesium, and are added as a hydroxide, chloride, acetate, sulphate, formate, oxide or nitrate salt to the composition of the present invention.

Diamine

In another preferred embodiment, the liquid cleaning composition of the present invention comprises a diamine or a mixture thereof as the pH buffer. The composition will preferably contain from about 0% to about 15%, preferably from about 0.1% to about 15%, preferably from about 0.2% to about 10%, more preferably from about 0.25% to about 6%, more preferably from about 0.5% to about 1.5% by weight of the total composition of at least one diamine.

Preferred organic diamines are those in which $pK_1$ and $pK_2$ are in the range of from about 8.0 to about 11.5, preferably in the range of from about 8.4 to about 11, even more preferably from about 8.6 to about 10.75. Preferred materials include 1,3-bis(methylamine)cyclohexane (pKa=from about 10 to about 10.5), 1,3-propane diamine ($pK_1$=10.5; $pK_2$=8.8), 1,6-hexane diamine ($pK_1$=11; $pK_2$=10), 1,3-pentane diamine (DYTEK EP®) ($pK_1$=10.5; $pK_2$=8.9), 2-methyl-1,5-pentane diamine (DYTEK A®) ($pK_1$=11.2; $pK_2$=10.0). Other preferred materials include primary/primary diamines with alkylene spacers ranging from $C_4$ to $C_8$. In general, it is believed that primary diamines are preferred over secondary and tertiary diamines. pKa is used herein in the same manner as is commonly known to people skilled in the art of chemistry: in an all-aqueous solution at 25° C. and for an ionic strength between about 0.1 to about 0.5 M. values. Reference can be obtained from literature, such as from "Critical Stability Constants: Volume 2, Amines" by Smith and Martel, Plenum Press, NY and London, 1975.

Chelant

R has been found that the addition of a chelant in the liquid cleaning composition of the present invention provides an unexpected improvement in terms of its cleaning capability. In a preferred embodiment, the composition of the present invention may comprise a chelant at a level of from about 0.1% to about 20%, preferably from about 0.2% to about 5%, more preferably from about 0.2% to about 3% by weight of total composition.

Suitable chelants can be selected from the group consisting of an amino carboxylate or a mixture thereof; an amino phosphonate or a mixture thereof; a polyfunctionally-substituted aromatic chelant or a mixture thereof; and mixtures thereof.

Preferred chelants for use herein are the amino acid based chelants, and preferably glutamic-N,N-diacetic acid (GLDA) and derivatives, and/or phosphonate based chelants, and preferably diethylenetriamine pentamethylphosphonic acid. GLDA (salts and derivatives thereof) is especially preferred according to the invention, with the tetrasodium salt thereof being especially preferred.

Also preferred are amino carboxylates including ethylenediaminetetra-acetate, N-hydroxyethylethylenediaminetriacetate, nitrilo-triacetate, ethylenediamine tetrapro-prionate, triethylenetetraaminehexacetate, diethylenetriaminepentaacetate, ethanoldi-glycine; and alkali metal, ammonium, and substituted ammonium salts thereof; and mixtures thereof; as well as MGDA (methylglycine-diacetic acid), and salts and derivatives thereof;

Other chelants include homopolymers and copolymers of polycarboxylic acids and their partially or completely neutralized salts, monomeric polycarboxylic acids and hydroxycarboxylic acids and their salts. Preferred salts of the above-mentioned compounds are the ammonium and/or alkali metal salts, i.e. the lithium, sodium, and potassium salts, and particularly preferred salts are the sodium salts.

Suitable polycarboxylic acids are acyclic, alicyclic, heterocyclic and aromatic carboxylic acids, in which case they contain at least about two carboxyl groups which are in each case separated from one another by, preferably, no more than about two carbon atoms. Polycarboxylates which comprise two carboxyl groups include, for example, water-soluble salts of, malonic acid, (ethyl enedioxy)diacetic acid, maleic acid, diglycolic acid, tartaric acid, tartronic acid and fumaric acid. Polycarboxylates which contain three carboxyl groups include, for example, water-soluble citrate. Correspondingly, a suitable hydroxycarboxylic acid is, for example, citric acid. Another suitable polycarboxylic acid is the homopolymer of acrylic acid. Preferred are the polycarboxylates end capped with sulphonates.

Further suitable polycarboxylates chelants for use herein include acetic acid, succinic acid, formic acid; all preferably in the form of a water-soluble salt. Other suitable polycarboxylates are oxodisuccinates, carboxymethyloxysuccinate and mixtures of tartrate monosuccinic and tartrate disuccinic acid such as described in U.S. Pat. No. 4,663,071.

Amino phosphonates are also suitable for use as chelant and include ethylenediaminetetrakis (methylenephosphonates) as DEQUEST. Preferably, these amino phosphonates do not contain alkyl or alkenyl groups with more than about 6 carbon atoms.

Polyfunctionally-substituted aromatic chelants are also useful in the composition herein, such as described in U.S. Pat. No. 3,812,044. Preferred compounds of this type in acid form are dihydroxydisulfobenzenes such as 1,2-dihydroxy-3,5-disulfobenzene.

Hydrotrope

The liquid cleaning composition of the present invention may optionally comprise a hydrotrope in an effective amount so that the composition is appropriately compatible in water. The composition of the present invention typically comprises from about 0% to about 15% by weight of the total composition of a hydrotropic, or mixtures thereof, preferably from about 1% to about 10%, most preferably from about 3% to about 6%. Suitable hydrotropes for use herein include anionic-type hydrotropes, particularly sodium, potassium, and ammonium xylene sulphonate, sodium, potassium and ammonium toluene sulphonate, sodium potassium and ammonium cumene sulphonate, and mixtures thereof, and related compounds, as disclosed in U.S. Pat. No. 3,915,903.

Polymeric Suds Stabilizer

The liquid cleaning composition of the present invention may optionally contain a polymeric suds stabilizer. These polymeric suds stabilizers provide extended suds volume and suds duration of the composition. The composition preferably contains from about 0.01% to about 15%, preferably from about 0.05% to about 10%, more preferably from about 0.1% to about 5%, by weight of the total composition of the polymeric suds booster/stabilizer.

These polymeric suds stabilizers may be selected from homopolymers of a (N,N-dialkylamino)alkyl ester and a (N,N-dialkylamino)alkyl acrylate ester. The weight average molecular weight of the polymeric suds booster, determined via conventional gel permeation chromatography, is from about 1,000 to about 2,000,000, preferably from about 5,000 to about 1,000,000, more preferably from about 10,000 to about 750,000, more preferably from about 20,000 to about 500,000, even more preferably from about 35,000 to about 200,000. The polymeric suds stabilizer can optionally be present in the form of a salt, either an inorganic or organic salt, for example the citrate, sulphate, or nitrate salt of (N,N-dimethylamino)alkyl acrylate ester.

One preferred polymeric suds stabilizer is (N,N-dimethylamino)alkyl acrylate ester, namely the acrylate ester represented by the formula (VII):

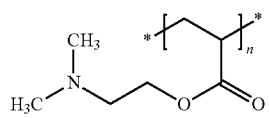

(VII)

Other preferred suds boosting polymers are copolymers of hydroxypropylacrylate/dimethyl aminoethylmethacrylate (copolymer of HPA/DMAM), represented by the formulae VIII and IX

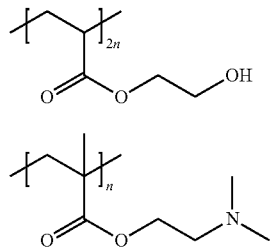

(VIII)

(IX)

Another preferred class of polymeric suds booster polymers are hydrophobically modified cellulosic polymers having a weight average molecular weight ($M_w$) below about 45,000; preferably between about 10,000 and about 40,000; more preferably between about 13,000 and about 25,000. The hydrophobically modified cellulosic polymers include water soluble cellulose ether derivatives, such as nonionic and cationic cellulose derivatives. Preferred cellulose derivatives include methylcellulose, hydroxypropyl methylcellulose, hydroxyethyl methylcellulose, and mixtures thereof.

EXAMPLES

Synthesis Examples

The amount of alkylating agent determines the amount of quaternization of the amino groups in the polymer, i.e. the amount of quaternized moieties.

The amount of the quaternized moieties can be calculated from the difference of the amine number in the non-quaternized amine and the quaternized amine.

The amine number can be determined according to the method described in DIN 16945.

Example 1

Synthesis of PEI600 EO40 with 25% quaternization a) PEI600+1EO/NH

In a 3.5 l autoclave 1328.5 g of a polyethyleneimine 600 (average molecular weight $M_w$ of 600) and 66.4 g water were heated to 80° C. and purged three times with nitrogen up to a pressure of 5 bar. After the temperature had been increased to 120° C., 1359.4 g ethylene oxide were added in portions up to 7 bar. To complete the reaction, the mixture was allowed to post-react for 2 h at 120° C. The reaction mixture was stripped with nitrogen and volatile compounds were removed in vacuo at 70° C. The temperature was increased to 90-110° C. and the mixture was dewatered for 2 hours in vacuo.

2688 g of polyethyleneimine 600 with 1 mole of ethylene oxide per mole NH were obtained as a yellow viscous oil (Amine value: 549 mg KOH/g; pH of a 1% by weight aqueous solution: 11.06).

b) PEI600+10EO/NH

In a 5 l autoclave 704.5 g of the product obtained in Example 1a) and 21.1 g of a 50% by weight aqueous solution of potassium hydroxide were heated to 80° C. and purged three times with nitrogen. The mixture was dewatered at 120° C. and a vacuum of 10 mbar for 2 h. After the vacuum had been removed with nitrogen, the temperature was increased to 145° C. and 3206.7 g ethylene oxide were added in portions up to 7 bar. To complete the reaction, the mixture was allowed to post-react for 2 h at 120° C. The reaction mixture was stripped with nitrogen and volatile compounds were removed in vacuo at 70° C.

3968 g of a polyethyleneimine 600 with 10 mole of ethylene oxide per mole NH bond were obtained as a yellow-brown viscous liquid (Amine value: 101.5 mg KOH/g; pH of a 10% by weight aqueous solution: 11.6).

c) PEI600+40EO/NH

In a 5 l autoclave 1084.6 g of the product obtained in Example 1b) was heated to 80° C. and purged three times with nitrogen. The mixture was dewatered at 120° C. and a vacuum of 10 mbar for 0.5 h. After the vacuum had been removed with nitrogen, the temperature was increased to 145° C. and 2927.6 g ethylene oxide were added in portions up to 7 bar. To complete the reaction, the mixture was allowed to post-react for 2 h at 120° C. The reaction mixture was stripped with nitrogen and volatile compounds were removed in vacuo at 70° C.

4030 g of a polyethyleneimine 600 with 40 mole of ethylene oxide per mole NH bond were obtained as a light brown solid (Amine value: 26.9 mg KOH/g; pH of a 10% by weight aqueous solution: 10.8; Viscosity (70° C.): 410 mPas).

d) PEI600+40EO/NH, 25% quaternized with dimethyl sulfate

In a 2 l reaction vessel 1700.0 g of the product from example 1c) was heated to 70-75° C. under a constant stream of nitrogen. 25.7 g dimethyl sulfate was added within 15 min. The reaction mixture was stirred for additional 2 h at 75° C.

1725.0 g of light brown solid were obtained (Amine value: 19.6 mg KOH/g; pH of a 10% by weight aqueous solution: 9.4; Viscosity (70° C.): 444 mPas).

Example 2

Synthesis of PEI600 EO62 with 25% Quaternization a) PEI600+1EO/NH

In a 3.5 l autoclave 1328.5 g of a polyethyleneimine 600 (average molecular weight $M_w$, of 600) and 66.4 g water were heated to 80° C. and purged three times with nitrogen up to a pressure of 5 bar. After the temperature had been increased to 120° C., 1359.4 g ethylene oxide were added in portions up to 7 bar. To complete the reaction, the mixture was allowed to post-react for 2 h at 120° C. The reaction mixture was stripped with nitrogen and volatile compounds were removed in vacuo at 70° C. The temperature was increased to 90-110° C. and the mixture was dewatered for 2 hours in vacuo.

2688.0 g of polyethyleneimine 600 with 1 mole of ethylene oxide per mole NH were obtained as a yellow viscous oil (Amine value: 549 mg KOH/g; pH of a 1% by weight aqueous solution: 11.06).

b) PEI600+10EO/NH

In a 5 l autoclave 704.5 g of the product obtained in Example 1a) and 21.1 g of a 50% by weight aqueous solution of potassium hydroxide were heated to 80° C. and purged three times with nitrogen. The mixture was dewatered at 120° C. and a vacuum of 10 mbar for 2 h. After the vacuum had been removed with nitrogen, the temperature was increased to 145° C. and 3206.7 g ethylene oxide were added in portions up to 7 bar. To complete the reaction, the mixture was allowed to post-react for 2 h at 120° C. The reaction mixture was stripped with nitrogen and volatile compounds were removed in vacuo at 70° C.

3968.0 g of a polyethyleneimine 600 with 10 mole of ethylene oxide per mole NH bond were obtained as a yellow-brown viscous liquid (Amine value: 101.5 mg KOH/g; pH of a 10% by weight aqueous solution: 11.6).

c) PEI600+62EO/NH

In a 3.5 l autoclave 247.8 g of the product obtained in Example 1b) was heated to 80° C. and purged three times with nitrogen. The mixture was dewatered at 120° C. and a vacuum of 10 mbar for 0.5 h. After the vacuum had been removed with nitrogen, the temperature was increased to 140° C. and 1116.3 g ethylene oxide were added in portions up to 7 bar. To complete the reaction, the mixture was allowed to post-react for 5 h at 120° C. The reaction mixture was stripped with nitrogen and volatile compounds were removed in vacuo at 70° C.

1410.0 g of a polyethyleneimine 600 with 62 mole of ethylene oxide per mole NH bond were obtained as a light brown solid (Amine value: 18.5 mg KOH/g; pH of a 10% by weight aqueous solution: 10.8)

d) PEI600+62 EO/NH, 25% Quaternized with Dimethyl Sulfate

In a 0.25 l reaction vessel 120.0 g of the product from example 1c) was heated to 70-75° C. under a constant stream of nitrogen. 1.26 g dimethyl sulfate was added within 15 min. The reaction mixture was stirred for additional 2 h at 75° C.

105.0 g of light brown solid were obtained (Amine value: 13.4 mg KOH/g; pH of a 10% by weight aqueous solution: 8.8).

Example 3

Synthesis of PEI600 EO72 with 25% Quaternization a) PEI600+72 EO/NH

In a 3.5 l autoclave 232.0 g of the product obtained in Example 1b) was heated to 80° C. and purged three times with nitrogen. The mixture was dewatered at 120° C. and a vacuum of 10 mbar for 0.5 h. After the vacuum had been removed with nitrogen, the temperature was increased to 140° C. and 1254.5 g ethylene oxide were added in portions up to 7 bar. To complete the reaction, the mixture was allowed to post-react for 5 h at 120° C. The reaction mixture was stripped with nitrogen and volatile compounds were removed in vacuo at 70° C.

1500.0 g of a polyethyleneimine 600 with 72 mole of ethylene oxide per mole NH bond were obtained as a light brown solid (Amine value: 16.27 mg KOH/g; pH of a 10% by weight aqueous solution: 10.0)

b) PEI600+72 EO/NH, 25% Quaternized with Dimethyl Sulfate

In a 0.25 l reaction vessel 120.0 g of the product from example 2a) was heated to 70-75° C. under a constant stream of nitrogen. 1.10 g dimethyl sulfate was added within 15 min. The reaction mixture was stirred for additional 2 to at 75° C.

107.0 g of light brown solid were obtained (Amine value: 12.3 mg KOH/9; pH of a 10% by weight aqueous solution: 8.9).

Test Methods

Molecular Weight Determination:

Molecular weight is determined as weight-average molecular weight ($M_w$) by gel permeation chromatography (GPC) using a serial configuration of the GPC columns HEMA Bio linear, 40·8 mm 10 µm, HEMA Bio 100, 300·8 mm, 10 µm, HEMA Bio 1000, 300·8 mm, 10 µm and HEMA Bio 10000, 300·8 mm, 10 µm, (obtained from PSS Polymer Standards Service GmbH, Mainz, Germany). The eluent is 1.5% aqueous formic acid, flow is 1 ml/min, injected volume is 20 µl, sample concentration is 1%. The method is calibrated with a Pullulan standard (MW 342-1660000 g/mol, obtained from PSS Polymer Standards Service GmbH, Mainz, Germany).

Method of Use

In the method aspect of this invention, soiled dishes are contacted with an effective amount, typically from about 0.5 mL to about 20 mL (per 25 dishes being treated), preferably from about 3 ml. to about 10 ml., of the liquid detergent composition of the present invention diluted in water. The actual amount of liquid detergent composition used will be based on the judgment of user, and will typically depend upon factors such as the particular product formulation of the composition, including the concentration of active ingredients in the composition, the number of soiled dishes to be cleaned, the degree of soiling on the dishes, and the like. The particular product formulation, in turn, will depend upon a number of factors, such as the intended market (i.e., U.S., Europe, Japan, etc.) for the composition product. Suitable examples may be seen below in Table I.

Generally, from about 0.01 ml. to about 150 ml., preferably from about 3 ml. to about 40 ml. of a liquid detergent composition of the invention is combined with from about 2000 ml. to about 20000 ml., more typically from about 5000 ml. to about 15000 ml. of water in a sink having a volumetric capacity in the range of from about 1000 ml. to about 20000 ml., more typically from about 5000 ml. to about 15000 ml. The soiled dishes are immersed in the sink containing the diluted compositions then obtained, where contacting the soiled surface of the dish with a cloth, sponge, or similar article cleans them. The cloth, sponge, or similar article may be immersed in the detergent composition and water mixture prior to being contacted with the dish surface, and is typically contacted with the dish surface for a period of time ranged from about 1 to about 10 seconds, although the actual time will vary with each application and user. The contacting of cloth, sponge, or similar article to the dish surface is preferably accompanied by a concurrent scrubbing of the dish surface.

Another method of use will comprise immersing the soiled dishes into a water bath or held under running water without any liquid dishwashing detergent. A device for absorbing liquid dishwashing detergent, such as a sponge, is placed directly into a separate quantity of undiluted liquid dishwashing composition for a period of time typically ranging from about 1 to about 5 seconds. The absorbing device, and consequently the undiluted liquid dishwashing composition, is then contacted individually to the surface of each of the soiled dishes to remove said soiling. The absorbing device is typically contacted with each dish surface for a period of time range from about 1 to about 10 seconds, although the actual time of application will be dependent upon factors such as the degree of soiling of the dish. The contacting of the absorbing device to the dish surface is preferably accompanied by concurrent scrubbing.

Shine Test Method

The formulation to be tested is diluted with tap water (water hardness: 15 gpg, temperature: 40° C.) in order to obtain a 10% solution of the original formulation. This solution is applied by a sponge to 3 drinking glasses, which are then rinsed for 10 seconds under running water (water hardness: 15 gpg; temperature: 40° C.). The glasses are stored vertically after rinsing and allowed to dry at ambient temperature (20° C.). After drying, the glasses are graded visually by two judges for shine on a 0 to 6 point scale (0=complete absence of streaks/spots; 6=extremely bad streaks/spots).

Viscosity Test Method

The viscosity of the composition of the present invention is measured on a Brookfield viscometer model # LVDVII+ at 20° C. The spindle used for these measurements is S31 with the appropriate speed to measure products of different viscosities; e.g., 12 rpm to measure products of viscosity greater than 1000 cps; 30 rpm to measure products with viscosities between 500 cps-1000 cps; 60 rpm to measure products with viscosities less than 500 cps.

Application Examples

Hand Dish Examples

Table 1 shows a known liquid cleaning composition which was prepared. The composition was prepared to show the shine benefit obtained in Hand Dishwashing by the addition of specific polyethyleneimine structures, as shown in Table 2.

TABLE 1

Cleaning Compositions before adding Alkoxylated Polyethyleneimine

| Examples | (% w/w) |
| --- | --- |
| Alkyl ethoxy sulfate $AE_xS$* | 16 |
| Amine oxide | 5.0 |
| $C_{9-11} EO_8$ | 5 |
| Ethylan 1008 ® | — |
| Lutensol ® TO 7 | — |
| GLDA[1] | 0.7 |
| DTPMP[2] | — |
| Sodium citrate | — |
| Solvent | 1.3 |
| Polypropylene glycol ($M_n$ = 2000) | 0.5 |
| Sodium chloride | 0.8 |
| Water | to balance |

*Number of carbon atoms in the alkyl chain is between 12 and 13; and x is between 0.5 and 2.

Ethylan 1008 ® is a nonionic surfactant based on a synthetic primary alcohol, commercially available from AkzoNobel.

Lutensol ® TO 7 is nonionic surfactant made from a saturated iso-$C_{13}$ alcohol.

Solvent is ethanol.

Amine oxide is coconut dimethyl amine oxide.

[1]Glutamic-N,N-diacetic acid

[2]Diethylenetriamine penta methylphosphonic acid

**Examples may have other optional ingredients such as dyes, pacifiers, perfumes, preservatives, hydrotropes, processing aids, salts, stabilizers, etc.

Table 2 shows a series of compositions prepared and tested for shine. The base formulation for all compositions was Formulation I from Table 1 above. Except for the control sample (2A), each of the compositions comprised 0.1% of an ethoxylated polyethyleneimine having the characteristics specified in the table. Shine testing was performed according to the method disclosed above. All compositions deliver good cleaning. Compositions 2A, 2B, 2C and 2D do not deliver good shine. Compositions 2E through 2I deliver good shine results.

TABLE 2

Shine Benefit from Addition of Selected Modified Polyethyleneimines into Cleaning Composition

|  | 2A (Control) | 2B | 2C | 2D | 2E | 2F | 2G | 2H | 2I |
| --- | --- | --- | --- | --- | --- | --- | --- | --- | --- |
| % Formulation I | 100% | 99.9% | 99.9% | 99.9% | 99.9% | 99.9% | 99.9% | 99.9% | 99.9% |
| % PEI | 0% | 0.1% | 0.1% | 0.1% | 0.1% | 0.1% | 0.1% | 0.1% | 0.1% |
| PEI Properties |  |  |  |  |  |  |  |  |  |
| PEI Backbone MW | — | 600 | 600 | 600 | 600 | 600 | 600 | 600 | 600 |
| EO Substitution | — | 24 | 20 | 30 | 30 | 30 | 50 | 50 | 50 |
| PO Substitution | — | 16 | 0 | 0 | 0 |  | 0 | 0 | 0 |
| % Quaternization | — | 0 | 8% | 10% | 25% | 50% | 10% | 25% | 50% |
| Results |  |  |  |  |  |  |  |  |  |
| Shine Grade | 4.0 | 3.0 | 2.0 | 2.0 | 1.2 | 1.5 | 1.2 | 1.0 | 1.0 |

Table 3 shows a further series of compositions prepared and tested for shine. The base formulation for all compositions was Formulation I from Table 1 above. Except for the control sample (3A), each of the compositions comprised 0.1% of an ethoxylated polyethyleneimine having the characteristics specified in the table. Shine testing was done according to the method disclosed above. Compositions 3B, 3C, 3D, and 3E comprise PEI structures which do not deliver a good shine result. Conversely, Composition 3F illustrates a preferred embodiment of the present invention and is especially good on shine, having an ethoxylation level of 40% and 27% quaternization.

TABLE 3

Shine Benefit from Addition of Selected Polyethyleneimines into Cleaning Composition

|  | 3A (Control) | 3B | 3C | 3D | 3E | 3F |
|---|---|---|---|---|---|---|
| % Formulation I | 100% | 99.9% | 99.9% | 99.9% | 99.9% | 99.9% |
| % PEI | 0% | 0.1% | 0.1% | 0.1% | 0.1% | 0.1% |
| PEI Properties |  |  |  |  |  |  |
| PEI Backbone MW | — | 600 | 600 | 600 | 600 | 600 |
| EO Substitution* | — | 10 | 10 | 10 | 10 | 40 |
| PO Substitution** | — | 16 | 16 | 16 | 16 | 0 |
| % Quaternization | — | 24% | 48% | 73% | 90% | 27% |
| Results |  |  |  |  |  |  |
| Shine Grade | 2.7 | 3.0 | 2.25 | 2.5 | 2.2 | 1.0 |

*moles of ethylene oxide per mole of NH
**moles of propylene oxide per mole of NH Table 4 shows a further series of compositions prepared and tested for shine. The base formulation for all compositions was Formulation from Table 1 above. Except for the control sample (4A), each of the compositions comprised 0.1% of an ethoxylated polyethyleneimine having the characteristics specified in the table. Shine testing was done according to the method disclosed above. Compositions 4B and 4C comprise PEI structures which do not deliver a good shine result. Conversely, Compositions 4D-4K illustrate preferred embodiments of the present invention and are especially good on shine.

TABLE 4

Shine Benefit from Addition of Selected Polyethyleneimines into Cleaning Composition

|  | 4A (Control) | 4B | 4C | 4D | 4E | 4F | 4G | 4H | 4I | 4J | 4K |
|---|---|---|---|---|---|---|---|---|---|---|---|
| % Formulation I | 100% | 99.9% | 99.9% | 99.9% | 99.9% | 99.9% | 99.9% | 99.9% | 99.9% | 99.9% | 99.9% |
| % PEI | 0% | 0.1% | 0.1% | 0.1% | 0.1% | 0.1% | 0.1% | 0.1% | 0.1% | 0.1% | 0.1% |
| PEI Properties |  |  |  |  |  |  |  |  |  |  |  |
| PEI Backbone MW |  | 600 | 600 | 600 | 600 | 1800 | 1800 | 600 | 600 | 1800 | 1800 |
| EO Substitution* |  | 7 | 7 | 62 | 72 | 30 | 50 | 62 | 72 | 30 | 50 |
| PO Substitution** |  | — | — | — | — | — | — | — | — | — | — |
| % Quaternization |  | 25% | 50% | 27% | 24% | 25% | 26% | 50% | 50% | 50% | 50% |
| Results |  |  |  |  |  |  |  |  |  |  |  |
| Shine Grade | 3.6 | 2.2 | 2.1 | 1.5 | 1.3 | 1.3 | 1.5 | 1.1 | 1.1 | 1.3 | 1.0 |

*moles of ethylene oxide per mole of NH
**moles of propylene oxide per mole of NH

Hand Dishwashing Detergent Composition Examples

| Examples (% w/w) | 1 | 2 | 3 | 4 | 5 |
|---|---|---|---|---|---|
| Alkyl ethoxy sulfate $AE_xS$* | 28.0 | 28.0 | 25.0 | 27.0 | 20.0 |
| Amine oxide | 7.0 | 7.0 | 7.0 | 5.0 | 5.0 |
| $C_{9-11} EO_8$ | — | — | — | 3.0 | 5.0 |
| Ethylan 1008 ® | — | — | 3.0 | — | — |
| Lutensol ® TO 7 | — | — | — | — | 5.0 |
| $GLDA^1$ | — | — | — | — | 1.0 |
| $DTPMP^2$ | — | — | — | — | 0.5 |
| $DTPA^3$ | — | — | 1.0 | — | — |
| $MGDA^4$ | — | — | — | 1.0 | — |
| Sodium citrate | — | — | 1.0 | — | 0.5 |
| Solvent | 2.5 | 2.5 | 4.0 | 3.0 | 2.0 |
| Polypropylene glycol ($M_n$ = 2000) | 1.0 | 1.0 | 0.5 | 1.0 | — |
| Sodium chloride | 0.5 | 0.5 | 1.0 | 1.0 | 0.5 |
| Quaternized Alkoxylated PEI according to the present invention | 0.1 | 0.2 | 0.1 | 0.1 | 0.5 |
| Water | to balance | to balance | to balance | to balance | to balance |

| Examples (% w/w) | 6 | 7 | 8 | 9 |
|---|---|---|---|---|
| Alkyl ethoxy sulfate $AE_xS$* | 13 | 16 | 17 | 15 |
| Amine oxide | 4.5 | 5.5 | 6.0 | 5.0 |
| $C_{9-11} EO_8$ | — | 2.0 | — | 5 |
| Ethylan 1008 ® | — | 2.0 | — | — |
| Lutensol ® TO 7 | 4 | — | 5 | — |
| $GLDA^1$ | 0.7 | 0.4 | 0.7 | 0.7 |
| $DTPMP^2$ | — | 0.3 | — | — |
| Sodium citrate | — | — | 0.2 | — |
| Solvent | 2.0 | 2.0 | 2.0 | 1.0 |
| Polypropylene glycol ($M_n$ = 2000) | 0.5 | 0.3 | 0.5 | 0.4 |
| Sodium chloride | 0.5 | 0.8 | 0.4 | 0.5 |
| Quaternized Alkoxylated PEI according to the present invention | 0.1 | 0.4 | 0.1 | 0.2 |
| Water | to balance | to balance | to balance | to balance |

| Examples (% w/w) | 10 | 11 | 12 | 13 |
|---|---|---|---|---|
| Alkyl ethoxy sulfate $AE_xS$* | 16 | 29 | 18 | 20 |
| Amine oxide | 5.0 | 7.0 | 6.0 | 6.5 |
| $C_{9-11} EO_8$ | 5 | — | — | 6.5 |
| Ethylan 1008 ® | — | — | — | — |
| Lutensol ® TO 7 | — | — | — | — |
| $GLDA^1$ | 0.7 | — | — | 1.0 |
| $DTPMP^2$ | — | — | — | — |
| Sodium citrate | — | — | 2.5 | — |
| Solvent | 1.3 | 4.0 | — | 2.0 |
| Polypropylene glycol ($M_n$ = 2000) | 0.5 | 1.0 | 1.0 | 0.4 |

| | | | | |
|---|---|---|---|---|
| Sodium chloride | 0.8 | 1.5 | 0.5 | 0.5 |
| Water | to balance | to balance | to balance | to balance |

*Number of carbon atoms in the alkyl chain is between 12 and 13; and x is between 0.5 and 2.
Ethylan 1008 ® is a nonionic surfactant based on a synthetic primary alcohol, commercially available from Akzo Nobel.
Lutensol ® TO 7 is nonionic surfactant made from a saturated iso-$C_{13}$ alcohol.
Solvent is ethanol.
Amine oxide is coconut dimethyl amine oxide.
[1]Glutamic-N,N-diacetic acid
[2]Diethylenetriamine penta methylphosphonic acid
**Examples may have other optional ingredients such as dyes, opacifiers, perfumes, preservatives, hydrotropes, processing aids, salts, stabilizers, etc.

Hard Surface Cleaning Example Compositions

The following examples will further illustrate the present invention. The compositions are made by combining the listed ingredients in the listed proportions (weight % unless otherwise specified). The following Examples are meant to exemplify compositions used in a process according to the present invention but are not necessarily used to limit or otherwise define the scope of the present invention.

| | A | B | C | D | E | F | G | H | I |
|---|---|---|---|---|---|---|---|---|---|
| Non ionic | | | | | | | | | |
| C9/11 EO 8 | 6.0 | 6.0 | 7.0 | | | 6.0 | 6.0 | 6.0 | 6.2 |
| C9/11 EO 5 | | | | 3.5 | | | | | |
| C12/14 EO21 | | | | 3.5 | | | | | |
| C11 EO 5 | | | | | 7.0 | | | | |
| Anionic | | | | | | | | | |
| NaLAS | 2.00 | 2.25 | 1.8 | | | | 1.80 | 2.25 | 1.80 |
| NAPS | | | | 3.1 | 3.0 | 3.0 | | | 3.1 |
| C12-14AS | | | | | | | | | |
| NaCS | | | | | | | | | |
| Co surfactants | | | | | | | | | |
| C12-14 AO | 1.50 | 1.25 | 1.50 | 3.9 | 2.0 | | 1.50 | 1.25 | 1.50 |
| C12-14 Betaine | | | | | 1.0 | 3.0 | | | |
| Quaternized Alkoxylated PEI according to the present invention | 0.1 | 0.3 | 0.5 | 0.1 | 0.2 | 0.2 | 0.4 | 0.05 | 0.3 |
| Thickeners | | | | | | | | | |
| HM-polyacrylate | 0.76 | 0.65 | 0.75 | | | | 0.70 | 0.65 | 0.65 |
| HM-HEC | | | | 0.6 | 0.8 | | | | |
| X gum | | | | | | 0.42 | | | |
| Buffer | | | | | | | | | |
| Na2CO3 | 0.77 | 0.4 | 0.75 | 0.1 | 0.3 | 0.2 | 0.75 | 0.4 | 0.75 |
| Citric Acid | 0.046 | 0.3 | 0.3 | 0.75 | 0.75 | 0.3 | 0.3 | 0.3 | 0.30 |
| Caustic | 0.46 | 0.76 | 0.72 | 0.5 | 0.5 | 0.3 | 0.65 | 0.65 | 0.60 |
| Suds control | | | | | | | | | |
| Fatty Acid | 0.40 | 1.0 | 1.0 | 0.20 | 0.50 | 0.50 | 0.40 | 0.40 | 1.0 |
| Branched fatty alcohols | | | | | | | | | |
| Isofol 12 | | 0.2 | 0.1 | 0.2 | 0.3 | 0.5 | | | 0.1 |
| Isofol 16 | | | | | | | | | |
| Chelants | | | | | | | | | |
| DTPMP | | 0.3 | 0.30 | | | 0.2 | | | 0.3 |
| DTPA | 0.25 | | | | | | 0.25 | 0.25 | |
| GLDA | | | | | | | | | |
| Solvents | | | | | | | | | |
| IPA | | | | | | 2.0 | | | |
| n-BPPP | | | | | 2.0 | | | | |
| N-BP | | | | 4.0 | 2.0 | | | 2.0 | |
| Minors and | up to | up to | up to | up to | up to | up to | up to | up to | up to |
| Water | 100% | 100% | 100% | 100% | 100% | 100% | 100% | 100% | 100% |
| pH | 10.6 | 10.5 | 10.3 | 9.5 | 9.0 | 10.0 | 10.3 | 10.5 | 10.3 |

$C_{9-11}$ $EO_5$ is a $C_{9-11}$ $EO_5$ nonionic surfactant commercially available from ICI or Shell. $C_{12,14}$ $EO_5$ is a $C_{12,14}$ $EO_5$ nonionic surfactant commercially available from Huls, A&W or Hoechst. $C_{11}$ $EO_5$ is a $C_{11}$ $EO_5$ nonionic surfactant. $C_{12,14}$ $EO_{21}$ is a $C_{12,14}$ $EO_{21}$ nonionic surfactant. NaPS is Sodium Paraffin sulphonate commercially available from Huts or Hoechst. NaLAS is Sodium Linear Alkylbenzene sulphonate commercially available from A&W. NaCS is Sodium Cumene sulphonate commercially available from A&W. Isalchem® AS is a $C_{12-13}$ sulphate surfactant commercially available from Sasol olefins and surfactants. $C_{12-14}$ AO is a $C_{12-14}$ amine oxide surfactant. $C_{12-14}$ Betaine is a $C_{12-14}$ betaine surfactant.

DMPEG is a polyethyleneglycol dimethylether. HM-HEC is a cetylhydroxethylcellulose. Isofol 12® is 2-butyl octanol commercially available from Condea. Isofol 16® is 2-hexyl decanol commercially available from Condea. n-BP is normal butoxy propanol commercially available from Dow Chemicals. IPA is isopropanol. n-BPP is butoxy propoxy propanol available from Dow Chemicals.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An ethoxylated polyethyleneimine having the general structure of formula (I):

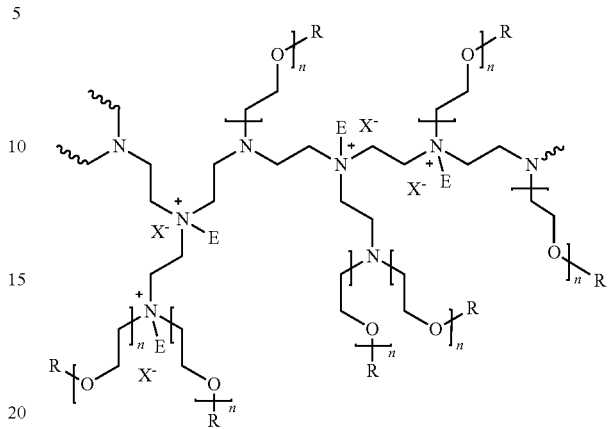

wherein n has a value which lies in the range of from 62 to 90, R is selected from hydrogen, a $C_1$-$C_4$ alkyl and mixtures thereof, E represents a $C_1$-$C_{12}$ alkyl moiety, $X^-$ represents a suitable water soluble counterion and the degree of quaternization of the nitrogen atoms present in the polyethyleneimine backbone lies in the range of from 1% to 50%.

2. The ethoxylated polyethyleneimine according to claim 1, wherein the polyethyleneimine backbone has a weight average molecular weight of from 400 to 10000 g/mol.

3. The ethoxylated polyalkylenimine polymer according to claim 1, wherein the polyethyleneimine backbone has a weight average molecular weight of from 400 to 6000 g/mol.

* * * * *